& Cummings

United States Patent [19]

Tarjan et al.

[11] Patent Number: 4,549,556
[45] Date of Patent: Oct. 29, 1985

[54] IMPLANTABLE LEAD

[75] Inventors: Peter P. Tarjan, Miami; Sandra L. Miller, No. Miami; John Martin, Miami, all of Fla.

[73] Assignee: Cordis Corporation, Miami, Fla.

[21] Appl. No.: 448,007

[22] Filed: Dec. 8, 1982

[51] Int. Cl.$^4$ .............................................. A61N 1/04
[52] U.S. Cl. .................................... 128/785; 128/786
[58] Field of Search ............................... 128/783–786, 128/419 P

[56] References Cited

U.S. PATENT DOCUMENTS

| | | | |
|---|---|---|---|
| 2,154,968 | 4/1939 | Alkio | 604/264 |
| 3,474,791 | 10/1969 | Benton | 128/785 |
| 3,664,347 | 5/1972 | Harmjanz | 128/786 |
| 3,995,623 | 12/1976 | Blake et al. | 128/419 P |
| 4,281,660 | 8/1981 | Fujiwara | 128/642 |
| 4,285,347 | 8/1981 | Hess | 128/786 |
| 4,409,994 | 10/1983 | Doring | 128/785 |
| 4,414,986 | 11/1983 | Dickhudt et al. | 128/785 |
| 4,419,819 | 12/1983 | Dickhudt et al. | 128/785 |

Primary Examiner—Lee S. Cohen
Assistant Examiner—Steven Falk
Attorney, Agent, or Firm—Lockwood, Alex, FitzGibbon & Cummings

[57] ABSTRACT

An implantable neural stimulator lead for introduction to and fixation in the epidural space of a patient includes an electrical conductor coated with a non-conductive coating and having a contact region thereon including an electrode for stimulating the patient's spinal cord through the dura. The contact region is located substantially intermediate the distal ends of the lead, whereby the lead may be installed and fixed in the epidural space by manipulation of both ends of the lead. A second surrogate lead is also provided for coupling to an end of the stimulator lead to enable the stimulator lead to be pulled into a position in the patient's body where stimulation is to be effected. One end of the surrogate lead includes a groove to facilitate snaring with a looped snare.

16 Claims, 12 Drawing Figures

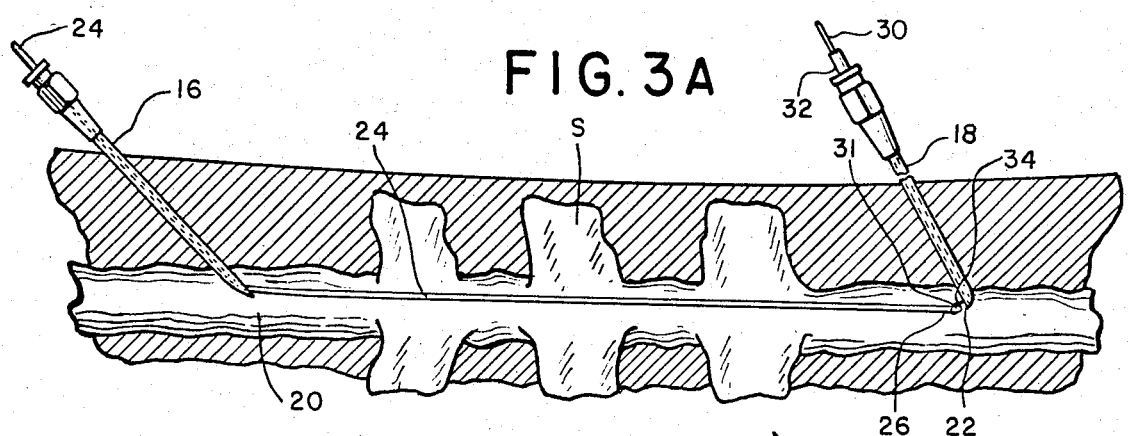
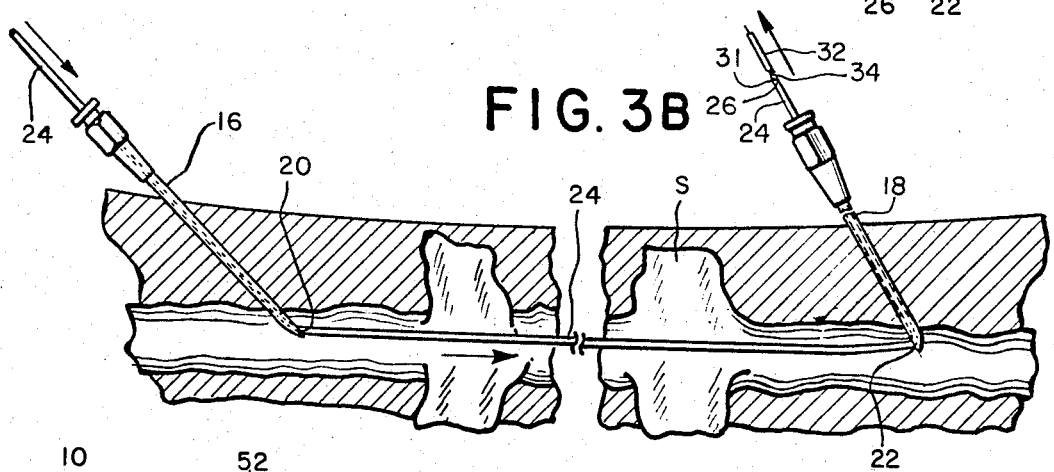
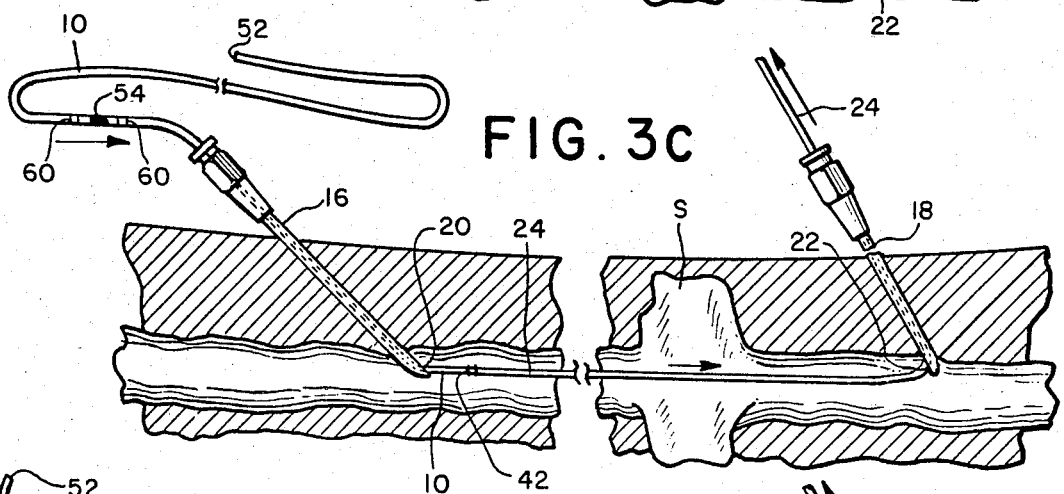
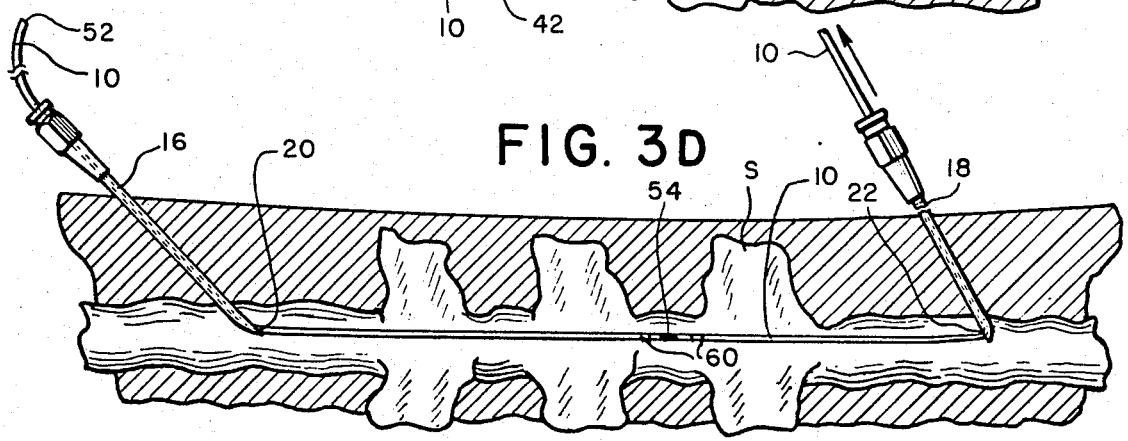

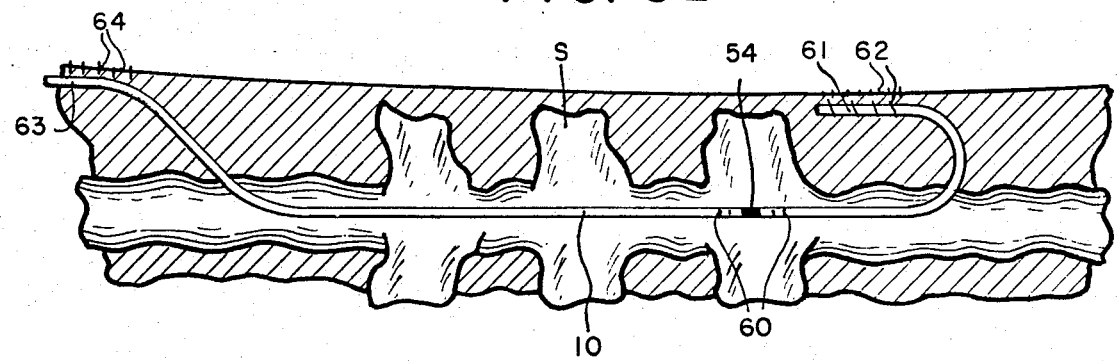
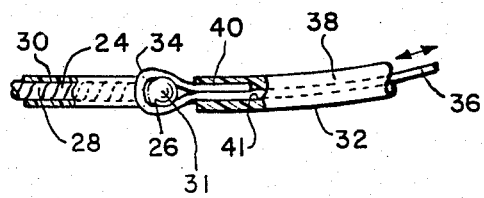
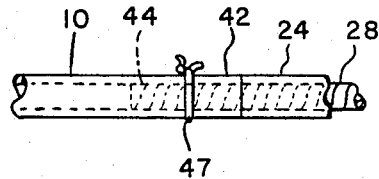
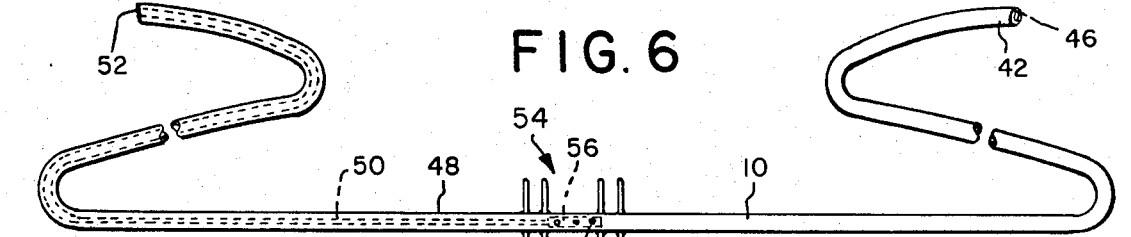
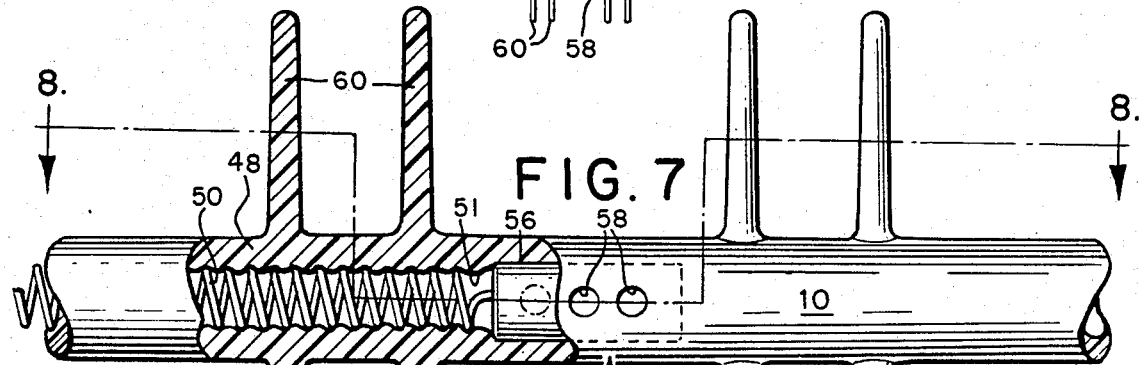
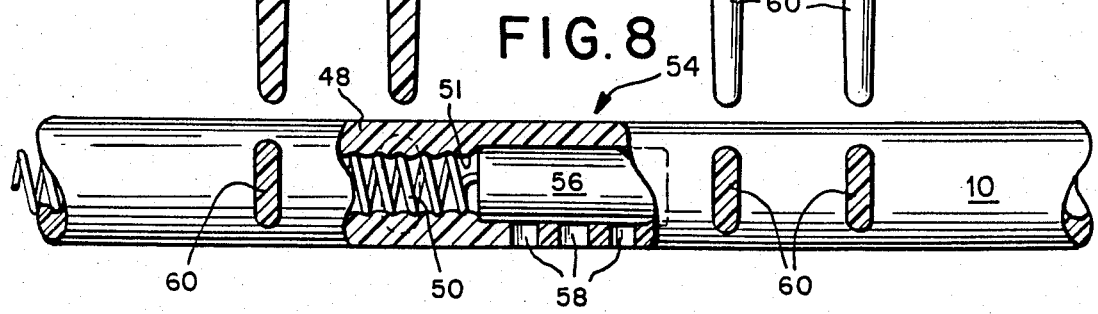

IMPLANTABLE LEAD

BACKGROUND AND SUMMARY OF THE INVENTION

The present invention relates to a conductive implantable lead and, more particularly, to a neural stimulator lead which may be installed and fixed in the epidural space of the spinal cord of a patient.

Neural stimulator electrodes and leads have been employed in the past which have been implanted in the epidural space of the spinal cord of a patient for stimulating selected locations along the spinal cord for such purposes as the relief of pain. One such lead is disclosed in U.S. Pat. No. 4,285,347 in which the leading distal end of the lead is axially moved along the epidural space in the spinal cord by passing the end through a Tuohy needle and pushing the end of the lead to the location on the dura where it is to stimulate the spinal cord. That lead has a configuration at its distal end and adjacent the stimulating electrode which may be deformed during installation of the lead by a stylet which passes through the lead to ease its introduction. Once the lead has been positioned as desired, the stylet is removed to cause the distal end of the lead to expand to minimize subsequent axial or lateral movement of the lead once it has been placed. In the lead disclosed in that patent, the leading distal end of the lead is inaccessibly located in the epidural space at all times during introduction and fixation and, thereby, is capable of being manipulated from only one end thereof.

Implantable leads incorporating the principles of the present invention enjoy several advantages over the prior neural stimulator leads. Implantable leads incorporating the principles of the present invention greatly facilitate the initial positioning of the lead electrodes with a minimum of effort and a minimum of trauma to the patient and essentially preclude the need for repositioning of the lead once it has been positioned. Implantable leads incorporating the principles of the present invention enable fixation of the lead at two points, thus minimizing the possibility of axial or lateral movement of the lead once it has been installed. Implantable leads incorporating the principles of the present invention may also eliminate the need for the use of a stylet during installation, thereby minimizing pain and trauma to the patient which might be associated with the installation and fixation procedure. Implantable leads incorporating the principles of the present invention enable precise control of the lead during installation and fixation by providing for manipulation simultaneously of both ends of the lead. Implantable leads incorporating the principles of the present invention may also include projections which stabilize the lead against accidental displacement once it has been properly placed at the location which is to be stimulated.

In one principal aspect of the present invention, an elongate, flexible, electrically conductive stimulator lead for implantation in the body of a patient includes an electrical conductor, a non-conductive coating covering the conductor and an electrode connected at one end of the conductor with at least a portion of the electrode being in electrical communication with the exterior of the coating to define an electrical contact region. The improvement in the lead comprises the contact region being located substantially intermediate the distal ends of said lead such that a substantial portion of the length of the lead extends in both directions from the electrode.

In another principal aspect of the present invention, the conductor of the aforementioned lead extends from the intermediately located electrode to a location adjacent one distal end of the lead.

In still another principal aspect of the present invention, the coating of the first mentioned lead comprises a tube having a lumen therein, a portion of the lumen containing the conductor, and an opening defined in the other distal end of the lead.

In still another principal aspect of the present invention, the coating of the first mentioned lead includes at least one flexible projection extending from the exterior of the coating adjacent the contact region for fixing the lead against displacement.

In still another principal aspect of the present invention, in the last mentioned lead the flexible projection comprises an elongate wing extending laterally from the coating and the length of the wing is approximately twice the diameter of the lead.

In yet another principal aspect of the present invention, the aforementioned leads are neural stimulator leads for stimulating the spinal cord of a patient, and the leads are sized for installation and fixation in the epidural space of the patient.

In still another principal aspect of the present invention, a combination for the introduction of a stimulator lead in the body of a patient comprises an electrically conductive stimulator lead, including a non-conductive coating and a conductor covered thereby, and an electrode in the stimulator lead in electrical communication with the exterior of the coating to define an electrical contact region. A second elongate flexible lead is provided and coupling means is provided for coupling at least one distal end of the stimulator lead with an end of the second lead to enable the stimulator lead to be pulled into a position in the patient's body where stimulation is to be effected.

In still another principal aspect of the present invention, the electrode as previously described is located substantially intermediate the distal ends of the stimulator lead and the conductor extends from the electrode to adjacent one distal end of the stimulator lead. The aforementioned coupling means is located adjacent the other distal end of the stimulator lead.

In still another principal aspect of the present invention, the aforementioned second lead includes groove means, such as bulbous means, at one end thereof to assist in snaring the end.

In still another principal aspect of the present invention, the last mentioned combination also includes snare means for tightening about the groove means and the snare means may comprise a movable loop.

These and other objects, features and advantages of the present invention will be clearly understood through a consideration of the following detailed description.

BRIEF DESCRIPTION OF THE DRAWINGS

In the course of this description, reference will frequently be made to the attached drawings in which:

FIG. 3A is a broken, partially cross-sectioned view of the patient's spinal cord and in which the surrogate lead has been snared;

FIG. 3B is a view similar to FIG. 3A, but in which the snared surrogate lead has been pulled through both of the Tuohy needles;

FIG. 3C is a view similar to FIG. 3B, but in which a neural stimulator lead incorporating the principles of the present invention has been coupled to the trailing end of the surrogate lead and has been pulled through one of the needles;

FIG. 3D is a view similar to FIG. 3C, but in which the neural stimulator lead has been positioned at its desired epidural location and its leading distal end has been drawn through the other needle;

FIG. 3E is a view similar to FIG. 3D, but in which the needles have been removed and the neural stimulator lead has been fixed;

FIG. 4 is an enlarged, partially broken cross-sectioned plan view showing the snare snaring the leading distal end of the surrogate lead similar to the installation step shown in FIG. 3A;

FIG. 5 is an enlarged, partially broken plan view of a suitable manner of coupling the trailing end of the surrogate lead to the leading distal end of the neural stimulator lead similar to the installation step shown in FIG. 3C;

FIG. 6 is an overall elevation view of a preferred embodiment of neural stimulator lead incorporating the principles of the present invention;

FIG. 7 is a partially broken elevation view of the electrical contact region of the lead shown in FIG. 6; and FIG. 8 is a partially broken plan view of the electrical contact region of the lead as viewed substantially along line 8—8 of FIG. 7.

DESCRIPTION OF THE PREFERRED EMBODIMENT

Figures 1, 2:
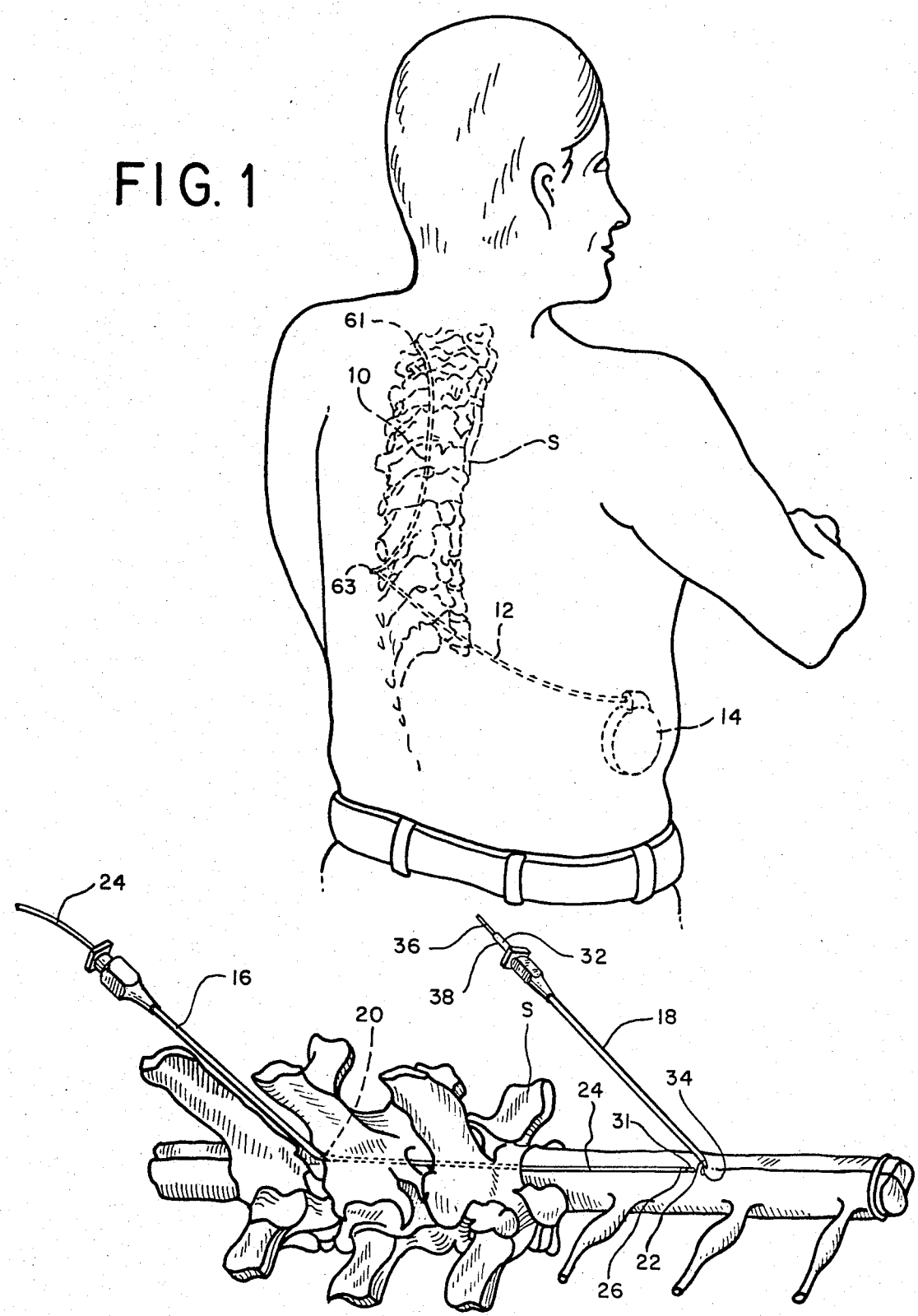
FIG. 1 is an overall perspective view of a patient in which a neural stimulator lead incorporating the principles of the present invention has been installed and fixed.
FIG. 2 is a broken view of a portion of the vertebrae and spinal cord of the patient in which a surrogate lead employed in the introduction of the lead of the present invention has been positioned in readiness to be snared.

The present invention is directed to an implantable lead and, more particularly, a neural stimulator lead 10 which may be introduced and fixed in the epidural space of the spinal cord of a patient. As shown in FIG. 1, the lead 10 is positioned in the epidural space in the patient's spinal column S and extends axially in that space. The lower distal end, or caudad end, of the lead is electrically connected, preferably subcutaneously, to a connector conductor 12. The connector conductor 12 also preferably extends subcutaneously and, in turn, is connected to a preferably subcutaneously implanted stimulator which generates electrical pulses or signals, as is known in the art, for stimulating one or more predetermined locations along the patient's spinal cord.

Installation of the neural stimulator lead 10 of the present invention begins by percutaneously positioning a pair of spaced Tuohy needles 16 and 18 through the skin of the patient as shown in FIG. 2. The construction of the Tuohy needles will not be described in detail as they are conventional and have been previously employed in a number of medical procedures, including the installation of neural stimulator leads. Each of the needles is hollow and may be of conventional cross-sectional shapes. One of the needles 16, the caudad or lower needle, is positioned as shown in FIG. 2 so that its lower open end 20 is located in the epidural space and pointing cephalad. The other needle 18, or cephalad needle, is also positioned so that its opening 22 is positioned in the epidural space and is then rotated as necessary so that its opening 22 faces caudad and the opening 20 of needle 16.

At this point a precursor surrogate lead 24 is preferably inserted through the upper end of the caudad needle 16, down through the needle 16, and the distal end 26 of the surrogate lead is pushed axially along the epidural space until it is adjacent the opening 22 in the cephalad needle 18.

The surrogate lead 24 is preferably formed of a helically wound wire 28 which is biologically compatible, such as stainless steel. The helical winding has the advantage of lying straight, thereby facilitating threading of the lead through the epidural space with a minimum of injury and trauma to the patient. The wire 28 is preferably encapsulated in a suitable biologically compatible coating 30, such as polyurethane, Teflon or Silastic, to further cushion the surrogate lead and minimize the possibility of injury or trauma to the patient. The distal end 26 of the surrogate lead is preferably grooved to facilitate snaring, as will next be discussed. The groove may either take the form of a bulbous shape 31, as best shown in FIG. 4, or, in the alternative, may be notched.

Once the distal end 26 of the surrogate lead 24 has been positioned adjacent the opening 22 in the cephalad needle 18, a snare 32, having a loop 34 at its leading end, is inserted through the cephalad needle 18 until the loop 34 just extends beyond the opening 22 of the needle. Entry of the loop into the epidural space will cause it to pitch downward slightly as shown in FIG. 2 to maximize exposure to the loop for threading of the distal end 26 of the surrogate lead 24 and its bulbous tip through the loop.

The snare 32 preferably comprises a single stainless steel wire 36 as shown in FIGS. 2 and 4 which preferably passes through a hollow encasing tubing 38. The wire 36 is preferably a straight wire as shown in FIG. 4, but may be helical, if desired. The tubing 38, likewise, is preferably formed of a suitable biologically compatible material, such as Silastic, Teflon polyethylene or polyurethane. Although the use of tubing 38 is shown, the tubing might be eliminated where the leading end of the surrogate lead 24 is notched or otherwise formed to cooperate with the snare loop 34. Where the tubing 38 is employed the loop 34 is formed at one end of the wire by looping the wire 36 back upon itself as shown in FIG. 4 and the distal end 40 of the wire is preferably fixed at the end of the tubing 38, such as by embedding the wire end 40 in the tubing as shown in FIG. 4. If the tubing 38 is eliminated, the wire 36 is bent back upon itself to form the loop.

The lumen 41 through the tubing 38 has a diameter which is preferably just large enough to allow axial movement of the wire 36 therein so as to allow selective enlargement or contraction of the size of the loop 34 to enable threading of the distal end 26 of the surrogate lead 24, and also snaring of that lead once it has been threaded through the loop. By embedding the distal end 40 of the wire 36 at the end of the tubing 38, only a single length of the wire need pass through the tubing, thus minimizing the diameter of the snare tubing 38. It will, however, be understood that the wire need not be embedded as shown in FIG. 4 and both legs of the loop wire may pass down the tubing, if tubing diameter is not a concern or the tubing may be eliminated altogether as previously discussed. The end of the wire 36 opposite the loop preferably extends beyond the exterior end of the tubing 38, as shown in FIGS. 2 and 3A, to allow manipulation of the wire to alter the size of the loop.

Once the distal end 26 of the surrogate lead 24 and its bulbous tip 31 have been snared by the loop 34 as shown in FIG. 3A, the snare 32 is withdrawn from the cephalad Tuohy needle 18 as shown in FIG. 3B. When the snare is withdrawn, the surrogate lead 24 now extends through both of the needles. Alternatively, if for some reason the snared surrogate lead end fails to pass through the opening of the cephalad needle 18, the needle may be withdrawn together with the snared leading end of the surrogate lead.

Either at this point in time or before the snare is withdrawn from needle 18, the leading distal end 42 of the neural stimulator lead 10 of the present invention may be coupled as shown in FIGS. 3C and 5 to the trailing end 44 of the surrogate lead 24. Such coupling may be accomplished by inserting the trailing end 44 of the surrogate lead into the opening 46 of the lead 10 as shown in FIG. 6. Opening 46 may be defined by the lumen through the neural stimulator lead which would otherwise contain the lead conductor. Such coupling occurs at a time when the trailing end 44 of the surrogate lead 24 still extends outside of the caudad needle 16 as shown in FIG. 3B. The coupling may be secured by tying off with a suture 47, as shown in FIG. 5, to prevent separation of the surrogate and neural stimulator leads as they are being drawn through the epidural space.

As shown particularly in FIGS. 6-8, a preferred embodiment of neural stimulator lead 10 incorporating the principles of the present invention preferably comprises an elongate flexible tube 48 formed of a biologically compatible material, such as Silastic, Teflon or polyurethane, and the tube 48 is preferably hollow over its entire length. One or more electrical conductors, such as the helical conductor 50 as shown in FIGS. 7 and 8, extends through the hollow lumen 51 through one side of the lead 10. Following installation, the end 52 of the conductor 50 is terminated with a suitable terminal (not shown) for coupling the lead 10 to the conductor 12. The other end of the conductor 50 terminates in an electrical contact region, generally 54 as shown in FIGS. 6-8, intermediate the length of the lead.

This contact region includes an electrode 56 which may be formed of platinum or other biologically compatible metal. The electrode 56 is positioned in lumen 51 in the tubing 48, but is exposed to the exterior of the tubing, such as by openings 58, to allow the body fluids to contact the electrode. The contact region 54 and its electrode 56 are positioned substantially intermediate the ends of the lead such that a substantial portion of the lead extends beyond the electrode in a direction opposite the conductor 50. This added length of lead enables the contact region to be positioned at the location in the patient's epidural space where it is to stimulate the spinal cord, but allows the additional length of the lead and, in particular its leading distal end 42, to extend from the cephalad needle 18 when the contact region is so positioned.

The neural stimulator lead 10 may also include one or more flexible projections adjacent the intermediate electrical contact region 54 to stabilize the electrode against axial or lateral displacement and fix the electrode in its desired implanted position at the location on the dura. By way of example, such projections may take the form of laterally extending flexible wings 60, as best shown in FIGS. 6-8. The wings 60 are very flexible to allow drawing of the lead through the epidural space during installation of the lead. The length of the wings 60 may vary, but is preferably on the order of about twice the diameter of the tube 48 of the lead 10. Although the wings 60 are shown as extending substantially perpendicular from the lead, it will be understood that they might extend at an acute angle thereto.

Returning to a description of the installation of the preferred embodiment of lead of the present invention, once the trailing end 44 of the surrogate lead 24 has been coupled to the neural stimulator lead 10, as shown in FIG. 5, the surrogate lead is withdrawn from the cephalad needle 18, as shown in FIG. 3C, and the neural stimulator lead 10 is drawn into the epidural space through the caudad needle 16.

Alternatively, the neural stimulator lead 10 may be coupled to the leading end of the surrogate lead 24 which extends from the cephalad needle 18. In this case, the surrogate lead 24 is pulled back through the cephalad and caudad needles 18 and 16, respectively, to withdraw the surrogate lead and to draw the neural stimulator lead from cephalad to caudad in the reverse direction. Whichever drawing procedure is used, drawing is continued until the electrical contact region 54 and its electrode 56 are positioned at the desired location in the epidural space. Control of the positioning of the lead 10 is greatly facilitated due to the fact that both ends extend from the respective Tuohy needles 16 and 18 when the contact region 54 and its electrode 56 are located near or at the location to be stimulated.

Once the electrode 56 is positioned in its desired location, the Tuohy needles 16 and 18 are both removed, if they had not been removed earlier. The leading distal end 42 of the stimulator lead 10 is cut to a suitable length to allow for some slight looping to relieve strain on the lead and to sever the surrogate lead 24 and its trailing end 44, as shown in FIG. 5, from the neural stimulator lead 10. The tubing opening 46 at the cut is preferably sealed by a suitable polymer or the like, either as made or at the time of cutting, to prevent entry of body fluids into the lead end of the lead 10. This cephalad end 61 of the lead 10 is then positioned subcutaneously and the lead and the incision is sutured by sutures 62, as shown in FIG. 3E, to fix the lead. The trailing caudad end 63 of the lead 10 is coupled, preferably subcutaneously, to conductor 12 and to the stimulator 14, both of which are also preferably subcutaneously located. The incision at the trailing caudad end 63 of the lead is also sutured, as by sutures 64 shown in FIG. 3E, to fix the caudad end 63 of the lead 10.

From the above description it will be seen that the neural stimulator lead 10 and its electrical contact region 54 may be readily and accurately initially positioned by manipulation of both ends of the lead 10. Moreover, it will be seen that the lead incorporating the principles of the present invention may eliminate the need altogether for the use of a stylet during installation and the potential disadvantages associated with such use and the need to reposition the lead once it is installed and fixed is substantially eliminated because the stimulator lead 10 may be secured at both ends once the lead has been positioned.

The above described installation and fixation of the lead is of course greatly facilitated by utilizing X-ray fluoroscopy, ultrasonic imaging and other known techniques during the installation and fixation. Accordingly, the various elements, such as the stimulator lead 10, the needles 16 and 18, the surrogate lead 24 and the snare 32 are all preferably formed of radiopaque material.

Although a single electrode 56 only is shown in the neural stimulator lead 10, the neural stimulator lead may include more than one electrode as desired. Moreover, even though the above described manner of installation and fixation has been described in terms of feeding the various components through the caudad needle 16 and removing the components through the cephalad needle 18, the direction of insertion and drawing may be reversed as desired.

It will also be understood that the embodiment of the present invention which has been described is merely illustrative of one of the applications of the principles of the present invention. Numerous modifications may be made by those skilled in the art without departing from the true spirit and scope of the invention.

What is claimed is:

1. An elongate flexible, electrically conductive neural stimulator lead including an electrical conductor for implantation in the spinal column of a patient and having leading and trailing ends, a non-conductive coating covering said conductor, and an electrode electrically connected to the conductor at one end thereof with at least a portion of said electrode being in electrical communication with the exterior of said coating to define an electrical contact region, wherein the improvement in said lead comprises:
   said leading and trailing ends each being of substantially uniform diameter;
   said contact region being located substantially intermediate said leading and trailing ends of said lead such that each of said leading and trailing ends is sufficiently long as to percutaneously exit the body at spaced locations therein when said contact region is positioned within the spinal column of a patient during implantation; and
   means adjacent said contact region for stabilizing said lead within the spinal column with the contact region within the spinal column and the leading and trailing ends percutaneously exiting the body.

2. The lead of claim 1, wherein said conductor extends from said intermediately located electrode to a location adjacent one of said ends of said lead.

3. The lead of claim 2, wherein said coating comprises a tube having a lumen therein, a portion of said lumen containing said conductor, and an opening defined in the other end of said lead.

4. The lead of claim 3, wherein said opening is defined by said lumen.

5. The lead of claim 1, wherein said coating comprises a tube having a lumen therein, said conductor and said electrode being positioned in said lumen, and means to electrically communicate said electrode with the exterior of said tube.

6. The lead of claim 5, wherein said means to communicate said electrode comprise at least one opening through the exterior surface of said tube.

7. The lead of claim 1, wherein said means adjacent said contact region for stabilizing said lead includes at least one flexible projection extending from the exterior of said coating adjacent said contact region for fixing the lead against displacement.

8. The lead of claim 7, wherein said flexible projection comprises an elongate wing extending laterally from said coating, the length of said wing being approximately twice the diameter of said lead.

9. A combination for the introduction of a neural stimulator lead in the spinal column of a patient, comprising:
   an electrically conductive stimulator lead having leading and trailing ends including a non-conductive coating and a conductor covered thereby, and an electrode in said stimulator lead electrically connected to said conductor, said electrode being in electrical communication with the exterior of said coating to define an electrical contact region, said leading and trailing ends being configured to percutaneously exit the body at spaced locations therein during implantation;
   means adjacent said contact region for stabilizing said lead within the spinal column;
   an elongate flexible lead; and
   coupling means for coupling one of said ends of said stimulator lead with an end of said flexible lead to enable said stimulator lead to be pulled into a position in the patient's spinal column where stimulation is to be effected.

10. The combination of claim 9, wherein said electrode is located substantially intermediate said ends of said stimulator lead and said conductor extends from said electrode to adjacent one of said ends of said stimulator lead, said coupling means being located adjacent the other end of said stimulator lead.

11. The combination of claim 9, wherein said flexible lead includes grooved means at the other end thereof to assist in snaring said other end.

12. The combination of claim 11, wherein said last mentioned means is a bulbous shaped.

13. The combination of claim 11, including in combination therewith, snare means for tightening about said grooved means.

14. The combination of claim 12, including in combination therewith, snare means for tightening about said bulbous shape.

15. The combination of claim 13, wherein said snare means comprises a movable loop.

16. The combination of claim 14, wherein said snare means comprises a movable loop.

* * * * *